(12) United States Patent
Berner

(10) Patent No.: US 7,852,492 B2
(45) Date of Patent: Dec. 14, 2010

(54) DEVICE FOR TOMOGRAPHIC SCANNING OBJECTS

(75) Inventor: Markus Berner, Niederhasli (CH)

(73) Assignee: Nectar Imaging S.R.L., Imola (BO) (IT)

( * ) Notice: Subject to any disclaimer, the term of this patent is extended or adjusted under 35 U.S.C. 154(b) by 161 days.

(21) Appl. No.: 12/288,262

(22) Filed: Oct. 17, 2008

(65) Prior Publication Data

US 2009/0103103 A1 Apr. 23, 2009

(30) Foreign Application Priority Data

Oct. 18, 2007 (CH) .................................... 1624/07

(51) Int. Cl.
*G01B 11/24* (2006.01)
(52) U.S. Cl. .......................... 356/605; 433/29; 433/215
(58) Field of Classification Search ......... 356/601–623; 250/237 G; 433/213–215, 223
See application file for complete search history.

(56) References Cited

U.S. PATENT DOCUMENTS

| | | | |
|---|---|---|---|
| 4,575,805 A * | 3/1986 | Moermann et al. .......... 700/163 |
| 4,837,732 A | 6/1989 | Brandestini et al. |
| 5,189,493 A | 2/1993 | Harding |
| 5,413,481 A * | 5/1995 | Goppel et al. ................ 433/214 |
| 5,714,832 A | 2/1998 | Shirrod et al. |
| 6,291,817 B1 * | 9/2001 | Kobayashi et al. ....... 250/237 G |
| 6,977,732 B2 * | 12/2005 | Chen et al. .................... 356/603 |
| 7,286,246 B2 * | 10/2007 | Yoshida ....................... 356/605 |
| 7,355,721 B2 | 4/2008 | Quadling et al. |
| 7,573,583 B2 * | 8/2009 | Quadling et al. ............. 356/602 |
| 2003/0179385 A1 * | 9/2003 | Fujiwara et al. ............. 356/605 |
| 2006/0103854 A1 * | 5/2006 | Franke et al. ................ 356/603 |
| 2006/0132802 A1 | 6/2006 | Chung et al. |
| 2007/0109559 A1 | 5/2007 | Babayoff et al. |

* cited by examiner

*Primary Examiner*—Hoa Q Pham
(74) *Attorney, Agent, or Firm*—Maginot, Moore & Beck LLP

(57) ABSTRACT

A device for tomographic scanning objects comprises a source of light for irradiating the object; a first grid arranged in the optical axis of the light beam so that a pattern of the first grid is projected on the object; an optical imaging assembly for imaging the object on a sensor; and a second grid provided in the optical axis of the reflected light beam having a pattern matching the first grid, through said second grid the reflected light beam having the pattern of the first grid being guided so that the sensor senses the light beam reflected by the object with a Moiré pattern resulting from overlying the pattern of the first grid and the pattern of the second grid. The device further comprises a means for moving the first grid and/or the second grid at a frequency causing fluctuations in the intensity of the resulting Moiré pattern.

20 Claims, 1 Drawing Sheet

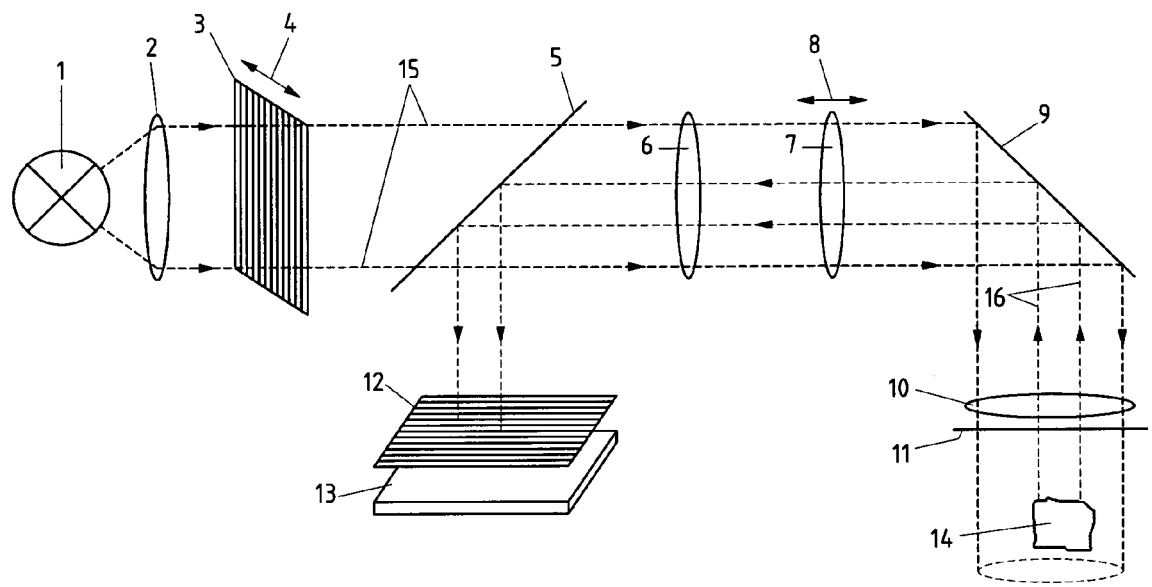

DEVICE FOR TOMOGRAPHIC SCANNING OBJECTS

BACKGROUND

The invention relates to a device for tomographic scanning objects, preferably dental teeth.

Devices and methods for scanning and processing the image data of objects by means of optical coherence tomography (OCT) are known.

A device for scanning and processing the image data of objects in the dental field by means of optical coherence tomography (OCT) reads, for example, is shown in WO 2004/100068 A3.

U.S. Pat. No. 4,837,732A relates to a method and an apparatus for 3D dental registration and display using a triangulation technique in which lines are projected and then observed at a different angle, the line distortion indicating the 3D shape. To enhance resolution the lines are moved. The method as known from U.S. Pat. No. 4,837,732A functions only with opaque specimens, this being the reason why the teeth have to be powdered before scanning. In addition to this, an object has to be illuminated at one angle and observed at another angle, resulting in scanning of very steep flanks not being possible.

Known furthermore are devices providing three-dimensional gauging of objects using Moiré patterns in which a pattern of a first grid is projected by means of a beam of light from a light source onto an object and the light beam reflected by the object is guided through a second grid provided in its optical axis and having the same pattern as the grid for sensing by a sensor so that the sensor senses the light beam reflected by the object with a Moiré pattern resulting from overlying the pattern of the first grid and the pattern of the second grid.

In such a device gauging the object is done by concluding the shape of the surface from the shape of the resulting Moiré pattern.

U.S. Pat. No. 5,714,832 A relates to a a device for precisely positioning a grating, the 3d shape being indicated from the shape of Moiré lines. The lines are shifted and to improve the signal quality narrow-band filtering is employed to obtain information as to the slope of the scanned area.

DE 41 36 002 A1 relates to a moiré contour imaging device involving scanning as is disclosed in the above document U.S. Pat. No. 5,714,832 A with LED illumination.

US 2006/0132802 A1 relates to a system for 3D reconstruction of a surface principle of an object surface employing scanning similar to that as already disclosed in the above document U.S. Pat. No. 4,837,732 A. Polarizers (two linear polarizers turned through 90°) are employed to suppress surface reflections.

Also known are devices which work on the principle of the laser confocal microscope (US 2007/0109559 A1).

In applications with diffuse or translucent surfaces there is the problem that the intensity of the Moiré pattern of the imaged object is very weak as compared to the other light reflected by the object.

SUMMARY

One object of the present invention is to provide a device for tomographic scanning objects which now assures good imaging of objects, such, as for example, teeth.

This object is achieved in accordance with the invention by a device for tomographic scanning objects, preferably teeth that comprises:

a source of light generating a light beam for irradiating the object;

a first grid arranged in the optical axis of the light beam downstream of the source of light through which the light beam is guided before irradiating the object so that a pattern of the first grid is projected on the object;

an optical imaging assembly for imaging the object on a sensor; and a second grid provided in the optical axis of the reflected light beam having a pattern matching the first grid, through the second grid the reflected light beam having the pattern of the first grid being guided so that the sensor senses the light beam reflected by the object with a Moiré pattern resulting from overlying the pattern of the first grid and the pattern of the second grid, wherein the device comprises furthermore a means for moving the first grid and/or the second grid, the motional frequency causing fluctuations in the intensity of the resulting Moiré pattern, and means for detecting fluctuations in intensity.

The Moiré pattern is only evident when the object is focused. To attain high resolution an optical assembly is accordingly employed, preferably having a large numerical aperture and thus a small depth of focus.

Moving at least one of the grids results in a movement of the Moiré pattern with the same motional frequency sensed by the sensor as fluctuations in the brightness or intensity of the Moiré pattern. The sensor thus senses a strong, constant signal overlying a weak alternating signal for the sensed fluctuations in intensity of the Moiré pattern.

The frequency of the alternating signal caused for better imaging of the object corresponds to the motional frequency relative to the grid(s) so that the signal can be filtered out by bandpass filtering, preferably narrow band filtering or Fourier analysis in thus enabling the signal strength of only the frequency of interest to be measured. Accordingly, despite unfavorable conditions as regards the depth of focus any point of a focal plane can be analyzed for an object as to whether a reflection from the object has occurred or not.

A scanning method in accordance with the invention is similar to that of a confocal microscope, resulting in a focused object producing a signal. Moving at least one of the grids is provided for in the invention to achieve a better signal-to-noise ratio. Preferably translucent specimens can be scanned, the invention achieving scanning of even perpendicular walls.

Preferably in accordance with the invention the patterns of the first grid and/or the second grid are line-like or checkered. Moving the first grid and/or the second grid is preferably done by continual rotation, it being preferred that the first grid and/or the second grid consist(s) of radial lines or multiple-turn spirals.

The second grid in the optical axis of the reflected light beam can be configured upstream of the sensor or by a pixel structure of the sensor.

The source of light employed in accordance with the invention can be a LED or a LED cluster. However, it is just as possible to make use of a single high-power laser. Where laser illumination is employed, the spatial coherence must be destroyed, for instance, by means of moved diffusers. The advantage of a laser is the exceptionally high efficiency of a laser light source (nowadays approx. 50%) as is unattainable by other light sources.

The light beam emitted by the source of light passes through the illuminating optical assembly, part of which is preferably part of the optical imaging assembly. Particularly the illuminating optical assembly comprises a collimating lens disposed between the source of light and the first grid for parallelizing the light beam emitted by the source of light, lenses for aligning the light beam, a mirror for deflecting the light beam in the direction of the object and a further lens for aligning the light beam.

The optical imaging assembly comprises in particular a lens for aligning the light beam reflected from the object, a mirror for deflecting the reflected light beam in the direction of the source of light, lenses for aligning the light beam reflected by the mirror and a further mirror for deflecting the reflected light beam in the direction of the sensor.

Inserted furthermore in the optical axis of the light beam upstream of the object or in the optical axis of the light beam reflected by the object upstream of the sensor is preferably a polarizing beam splitter to achieve a separation between the light beam irradiating the object and the reflected light beam in thus suppressing interference. In this case there is also inserted upstream of the object a λ/4 delay plate to rotate the polarization direction of the reflected light beam through 90° relative to the light beam irradiating the object.

The sensor may be a line sensor with which the object is sensed in one direction.

The device in accordance with the invention is intended for scanning the object particularly in two directions, all reflections to be sensed being found in a single plane.

The sensor may be an image sensor capable of sensing a plurality of locations of the object simultaneously. This image sensor is preferably a pixel image smart sensor which in addition to sensing a plurality of locations of the object is also capable of implementing preprocessing to detect fluctuations in the intensity produced by the moved Moiré pattern.

Included in the device in accordance with the invention is preferably a further means for moving a lens of the illuminating optical assembly for setting the focal plane in which the object is detected.

Provided furthermore is preferably a data processor for computing the surface of the object on the basis of the tomography data sensed by the sensor.

The device and at least part of the data processor are provided particularly in a scanner unit designed as a handy instrument for intraoral dental scanning.

The cited and further features and details of the invention will become clearer to a person skilled in the art from the following detailed description and enclosed drawing depicting features of the present invention by way of an example and wherein the sole

DESCRIPTION OF THE FIGURE

FIG. 1 is a diagrammatic illustration of the basic configuration of a device in accordance with the present invention.

DESCRIPTION OF THE EMBODIMENTS

The present invention will now be explained in detail by way of a preferred embodiment with reference to the attached drawing. The sole FIGURE shows the configuration in principle of the device for tomographic scanning objects, preferably dental teeth in accordance with the invention.

Referring now to FIG. 1 there is illustrated how the device for tomographic scanning objects comprises the following: a light source 1 generating a light beam 15 for irradiating the object 14; a first grid 3 disposed in the optical axis of the light beam 15 downstream of the light source 1, the light beam 15 being guided by the first grid 3 before irradiating the object 14 so that a pattern of the first grid 3 is projected on the object 14; an optical imaging assembly 5, 6, 7, 9, 10 for imaging the object 14 on a sensor 13; and inserted in the optical axis of the reflected light beam 16 a second grid 12 with a pattern matching the first grid 3, the reflected light beam 16 having a pattern of the first grid 3 being guided through the second grid 12 so that the sensor 13 senses the reflected light beam 16 reflected from the object 14 with a Moiré pattern resulting from overlying the pattern of the first grid 3 and the pattern of the second grid 12.

The light source 1 of the device in accordance with the invention can be a LED or a LED cluster.

The light beam 15 emitted by the light source 1, before impinging the object 14, passes through an optical illuminating assembly 2, 6, 7, 9, 10. As shown in FIG. 1 this optical illuminating assembly 2, 6, 7, 9, 10 comprises a collimating lens 2 disposed between the light source 1 and the first grid 3 for parallel rendering of the light beam 15 emitted by the light source 1, lenses 6, 7 for aligning the light beam 15, a mirror 9 for deflecting the light beam 15 in the direction of the object 14 and a further lens 10 for aligning the light beam 15.

The optical imaging assembly 5, 6, 7, 9, 10 as shown in the FIGURE comprises a lens 10 for aligning the reflected light beam 16 reflected by the object 14, a mirror 9 for deflecting the reflected light beam 16 in the direction of the light source 1, lenses 7, 6 for aligning the reflected light beam 16 reflected by the mirror 9 and a further mirror 5 for deflecting the reflected light beam 16 in the direction of the sensor 13. The mirror 5 in this case is a semi-transparent mirror.

Thus, part of the optical illumination assembly 2, 6, 7, 9, 10 is simultaneously part of the optical imaging assembly 5, 6, 7, 9, 10. This makes for a compact, cost-effective configuration and shows the advantage of eliminating distortion when projecting a pattern on the object by using the same optical assembly for the reflected light beam. However, illumination of the object is partly reflected back as gloss and attains the sensor as interference light. To eliminate sensor interference by this unwanted light there is inserted furthermore in the optical axis of the light beam 15 upstream of the object 14 and/or in the optical axis of the reflected light beam 16 reflected by the object 14 upstream of the sensor 13 a polarizing beam splitter 5 as a semi-transparent mirror as well as a circular polarizer 11. The circular polarizer 11 as shown in FIG.1 may be, for example, a λ/4 delay plate for attaining in a double pass a polarization direction of the reflected light beam 16 turned through 900 relative to the light beam 15 illuminating the object 14.

In the FIGURE the second grid 12 in the optical axis of the reflected light beam 16 is shown disposed upstream of the sensor 13, but it may also be configured by a pixel structure of the sensor 13. The patterns of the first grid 3 and of the second grid 12 may be line-like or checkered.

In accordance with the invention the device as shown in the FIGURE comprises furthermore a moving means 4 which moves the first grid 3, the frequency of the movement causing fluctuations in the intensity of the resulting Moiré pattern. The moving means 4 can also be provided such that it moves the second grid 12 alternatingly or additionally. The movement can be oscillating or continuous.

In an oscillating movement the first grid 3 and the second grid 12 are patterned linearly or checkered. But any other pattern is also conceivable, resulting in changes in the intensity by shifting pattern overlap.

In a continuous movement, for example, instead of the first grid 3 shown oscillating in the FIGURE a disc having radial lines can be rotated. Then, instead of the second grid 12 a pattern can be selected corresponding to the corresponding section on the disc.

Where a rotating disc is employed the Archimedes spiral proves to be a particularly suitable pattern. In such a spiral the line spacing is constant and independent of the radial position of the disc, resulting in the resolution of the scanner being the same everywhere in the image.

Such a spiral may also be configured multi-turn. By suitably selecting the number of lines of the spiral the rotational speed of the disc for a certain line frequency can be tweaked to a range which is favorable for driving the disc.

Moving at least one of the first and second grids 3 and 12 moves the Moiré pattern with the same motional frequency sensed by the sensor 13 as fluctuations in brightness or intensity. The sensor 13 thus senses a strong constant signal overlying a weak alternating signal for the sensed fluctuations in intensity of the Moiré pattern. In an oscillating motion the frequency at which the lines are moved equals the frequency of oscillation whereas in a continual motional the frequency at which the lines are moved equals the line frequency, in other words line speed divided by line spacing. The following makes mention of only the motional frequency. The frequency of the alternating signal caused for a better sensing of the object 14 corresponds to the motional frequency relative to the grid(s) 3, 12 and thus this alternating signal can be filtered out by means of bandpass filtering, preferably narrow band filtering or Fourier analysis and the signal strength only of the frequency of interest measured. Accordingly, in accordance with the invention despite unfavorable conditions as regards the depth of focus an object can be analyzed at each point in focal plane as to whether reflection from the object has occurred or not.

The device as shown in the FIGURE comprises a further means 8 for moving a lens 7 of the optical illumination assembly 2, 6, 7, 9, 10 for setting the focal plane in which the object 14 is detected.

Since scanning is required at a high rate (for example 10 scans per second) the lens 7 too needs to be moved fast. Because the apparatus is intended to be small and handy, the corresponding forces of acceleration are tangible and result in unwanted vibrations. These forces of acceleration are compensated by a counterweight moved contrary to the lens 7, i.e. the resulting reaction forces are zeroed by suitably selecting the counterweight.

The sensor 13 may be a line sensor for sensing the object 14 in one direction.

By means of the device in accordance with the invention sensing the object 14 is done preferably in two directions, all detectable reflections of the object being found in a single focal plane.

The sensor 13 may be an image sensor capable of sensing a plurality of locations of the object 14 simultaneously. This sensor 13 is preferably a pixel image smart sensor which in addition to sensing a plurality of locations of the object 14 is also capable of implementing preprocessing to detect fluctuations in the intensity produced by the moved Moiré pattern.

In accordance with the invention the device comprises a data processor for computing the surface of the object 14 on the basis of the tomography data sensed by the sensor 13. The device and at least part of the data processor are provided particularly in a scanner unit designed as a handy instrument for intraoral dental scanning.

When in a device for tomographic scanning a large aperture needs to be used for reasons of efficiency, no optical coherence tomography can be employed because then an interference pattern on the sensor has several periods on a pixel of a sensor and intensity stripes cancel each other out.

When scanning large objects using optical coherence tomography the aperture at the sensor side is large and also when scanning translucent bodies, such as dental teeth, the signal strength is relatively weak, thus making a large aperture mandatory.

This problem does not exist when using the device in accordance with the invention with parallel optical focal point tomography (pOFPT) and furthermore, because of there being no interferometer, the system is rugged. Scanning speed and modulation frequency are independent of each other, permitting a higher scanning speed. As a last advantage the device in accordance with the invention requires no reference arm.

The nature of the signals is, however, very similar as in an OCT apparatus, an example of a signal at the point where the object is in focus being an alternating signal. It is because of this similarity in the signals that in pOFPT the same electronics can be used for the analyzer as in OCT, especially also the pixel image smart sensor. Suppressing the unwanted signal is much more difficult with a signal as materializes in a laser contact focal microscope, because of the missing alternating signal. On top of this, laser contact focal microscopes are very much more problematic to realize.

The present invention thus provides a device for tomographic scanning objects, preferably dental teeth, which now makes it possible to find horizontal slices of an object simply and speedily in obtaining three-dimensional surfaces of the object with these slices. The device also permits obtaining information from the interior of a semitransparent body.

The invention claimed is:

1. A device for tomographic scanning objects, such as dental teeth, said device comprising:
    a source of light (1) generating a light beam (15) for irradiating the object (14);
    a first grid (3) arranged in the optical axis of the light beam (15) downstream of the source of light (1) through which the light beam (15) is guided before irradiating the object (14) so that a pattern of the first grid (3) is projected on the object (14);
    an optical imaging assembly (5, 6, 7, 9, 10) for imaging the object (14) on a sensor (13);
    a second grid (12) provided in the optical axis of the light beam (15) reflected from the object having a pattern matching the first grid (3), through said second grid (12) the reflected light beam (16) having the pattern of the first grid (3) being guided so that the sensor (13) senses the light beam (16) reflected by the object (14) with a Moiré pattern resulting from overlying the pattern of the first grid (3) and the pattern of the second grid (12);
    means (4) for moving either or both the first grid (3) and the second grid (12) at a frequency causing fluctuations in the intensity of the resulting Moiré pattern; and
    means for detecting fluctuations in the intensity including a bandpass filter associated with said sensor and tuned to said frequency.

2. The device as set forth in claim 1, wherein said bandpass filter uses, one or more of narrow band filtering and Fourier analysis.

3. The device as set forth in claim 1, characterized in that the patterns of either or both the first grid (3) and the second grid (12) are line-like or checkered.

4. The device as set forth in claim 1, characterized in that moving either or both the first grid and the second grid is done by continual rotation.

5. The device as set forth in claim 4, characterized in that either or both the first grid and the second grid consist(s) of radial lines or multiple-turn spirals.

6. The device as set forth in claim 1, characterized in that the second grid (12) in the optical axis of the reflected light beam (16) is configured upstream of the sensor (13) or by a pixel structure of the sensor (13).

7. The device as set forth in claim 6, characterized in that the optical illuminating assembly (2, 6, 7, 9, 10) comprises a collimating lens (2) disposed between the source of light (1) and the first grid (3) for parallelizing the light beam (15) emitted by the source of light (1), lenses (6, 7) for aligning the light beam (15), a mirror (9) for deflecting the light beam (15) in the direction of the object (14) and a further lens (10) for aligning the light beam (15).

8. The device as set forth claim 1, characterized in that the light source (1) is a LED or LED cluster.

9. The device as set forth in claim 1, characterized in that the light source (1) is single laser, particularly a high-power laser, the spatial coherence being destroyed by means of at least one movable diffusor.

10. The device as set forth in claim 1, characterized in that the light beam (15) emitted by the source of light (1) passes through an optical illuminating assembly (2, 6, 7, 9, 10) which is part of the optical imaging assembly (5, 6, 7, 9, 10).

11. The device as set forth in claim 1, characterized in that optical imaging assembly (5, 6, 7, 9, 10) comprises a lens (10) for aligning the light beam (16) reflected from the object (14), a mirror (9) for deflecting the reflected light beam (16) in the direction of the source of light (1), lenses (7, 6) for aligning the light beam (16) reflected by the mirror and a further mirror (5) for deflecting the reflected light beam (16) in the direction of the sensor (13).

12. The device as set forth in claim 1, characterized in that the sensor (13) is a line sensor with which the object (14) is sensed in one direction.

13. The device as set forth in claim 1, characterized in that scanning the object (14) is done in two directions, all reflections to be sensed being found in a single focal plane.

14. The device as set forth in claim 1, characterized in that the sensor (13) is an image sensor capable of sensing a plurality of locations of the object (14) simultaneously, the image sensor (13) being a pixel image smart sensor which in addition to sensing a plurality of locations of the object (14) is also capable of implementing preprocessing to detect fluctuations in the intensity produced by the moved Moiré pattern.

15. The device as set forth in claim 1, characterized in that a further means (8) for moving a lens (7) of the optical illuminating assembly (2, 6, 7, 9, 10) is provided for setting the focal plane in which the object (14) is detected.

16. The device as set forth in claim 1, characterized in that a data processor is provided for computing the surface of the object (14) on the basis of the tomography data sensed by the sensor (13).

17. The device as set forth in claim 1, characterized in that the device and at least part of the data processor are provided particularly in a scanner unit designed as a handy instrument for intraoral dental scanning.

18. A device for tomographic scanning objects, such as dental teeth, said device comprising:
- a source of light (1) generating a light beam (15) for irradiating the object (14);
- a circular polarizer (11) in the optical axis of the light beam (15) upstream of the object;
- a first grid (3) arranged in the optical axis of the light beam (15) downstream of the source of light (1) through which the light beam (15) is guided before irradiating the object (14) so that a pattern of the first grid (3) is projected on the object (14);
- an optical imaging assembly (5, 6, 7, 9, 10) for imaging the object (14) on a sensor (13);
- a second grid (12) provided in the optical axis of the reflected light beam (15) having a pattern matching the first grid (3), through said second grid (12) the reflected light beam (16) having the pattern of the first grid (3) being guided so that the sensor (13) senses the light beam (16) reflected by the object (14) with a Moiré pattern resulting from overlying the pattern of the first grid (3) and the pattern of the second grid (12);
- a polarizing beam splitter (5) inserted in the optical axis of the light beam (16) reflected by the object (14) upstream of the sensor (13);
- means (4) for moving either or both the first grid (3) and the second grid (12) at a frequency causing fluctuations in the intensity of the resulting Moiré pattern; and
- means for detecting fluctuations in the intensity.

19. The device as set forth in claim 18, wherein said means for detecting fluctuations in intensity includes a bandpass filter tuned to said frequency.

20. The device as set forth in claim 18, characterized in that a further means (8) for moving a lens (7) of the optical illuminating assembly (2, 6, 7, 9, 10) is provided for setting the focal plane in which the object (14) is detected.

* * * * *